(12) United States Patent
Matsui et al.

(10) Patent No.: US 8,507,467 B2
(45) Date of Patent: Aug. 13, 2013

(54) TRANSDERMALLY ABSORBABLE PREPARATION

(75) Inventors: Rakan Matsui, Yokohama (JP); Osamu Ueda, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 465 days.

(21) Appl. No.: 12/677,388

(22) PCT Filed: Sep. 10, 2008

(86) PCT No.: PCT/JP2008/002493
§ 371 (c)(1),
(2), (4) Date: Mar. 10, 2010

(87) PCT Pub. No.: WO2009/037813
PCT Pub. Date: Mar. 26, 2009

(65) Prior Publication Data
US 2010/0210613 A1 Aug. 19, 2010

(30) Foreign Application Priority Data
Sep. 20, 2007 (JP) ................................. 2007-243555

(51) Int. Cl.
| | | |
|---|---|---|
| *A61K 31/57* | (2006.01) | |
| *A61K 31/565* | (2006.01) | |
| *A61K 31/568* | (2006.01) | |
| *A61P 5/24* | (2006.01) | |
| *A61P 5/30* | (2006.01) | |
| *A61P 5/26* | (2006.01) | |

(52) U.S. Cl.
USPC ............................ 514/178; 514/177; 514/182

(58) Field of Classification Search
USPC .......................................... 514/178, 177, 182
See application file for complete search history.

(56) References Cited

U.S. PATENT DOCUMENTS

| | | | | |
|---|---|---|---|---|
| 4,685,911 | A | * 8/1987 | Konno et al. | 424/450 |
| 4,906,475 | A | * 3/1990 | Kim | 424/449 |
| 5,296,235 | A | 3/1994 | Sawayanagi et al. | |
| 5,820,878 | A | 10/1998 | Hirano et al. | |
| 5,891,462 | A | 4/1999 | Carrara | |
| 5,968,919 | A | 10/1999 | Samour et al. | |

FOREIGN PATENT DOCUMENTS

| | | |
|---|---|---|
| JP | 60-16917 | 1/1985 |
| JP | 4-103528 | 4/1992 |
| JP | 4-346922 | 12/1992 |
| JP | 5-25038 | 2/1993 |
| JP | 9-176049 | 7/1997 |
| JP | 10-72351 | 3/1998 |
| JP | 10-72353 | 3/1998 |
| JP | 3086288 | 7/2000 |
| JP | 2001-505930 | 5/2001 |
| JP | 2007-210941 | 8/2007 |
| WO | 96/15776 | 5/1996 |
| WO | WO96/19976 | * 7/1996 |

OTHER PUBLICATIONS

Espace Patent Abstract for JP Publication No. 4346922 published Dec. 2, 1992, one page.
Espace Patent Abstract for JP Publication No. 2001505930 published May 8, 2001, one page.
Espace Patent Abstract for JP Publication No. 10072351 published Mar. 17, 1998, one page.
Espace Patent Abstract for WO Publication No. 9615776 published May 30, 1996, one page.
Chinese Office Action 100034 dated Apr. 25, 2011, Application No. 200880107270.5.
International Search Report for corresponding PCT/JP2008/002493 mailed Oct. 28, 2008, three pages.
espacenet Patent Abstract for Japanese Publication No. 10072353 published Mar. 17, 1998, one page.
espacenet Patent Abstract for Japanese Publication No. 2007210941 published Aug. 23, 2007, one page.
espacenet Patent Abstract for Japanese Publication No. 3086288 published Sep. 11, 2000, one page.
espacenet Patent Abstract for Japanese Publication No. 4103528 published Apr. 6, 1992, one page.
espacenet Patent Abstract for Japanese Publication No. 60016917 published Jan. 28, 1985, one page.
espacenet Patent Abstract for Japanese Publication No. 9176049 published Jul. 8, 1997, one page.
Frank Z. Stanczyk et al. "Percutaneous administration of progesterone: blood levels and endometrial protection," Menopause, vol. 12, No. 2, 2005, pp. 232-237.

* cited by examiner

*Primary Examiner* — San-Ming Hui
*Assistant Examiner* — Kathrien Cruz
(74) *Attorney, Agent, or Firm* — Rankin, Hill & Clark LLP

(57) ABSTRACT

A transdermally absorbable preparation comprises a natural type sex hormone, a polyoxyethylene oleyl ether having a molar number of ethylene oxide units added of 20, at least two kinds of oily ingredients selected from the group consisting of diisopropyl adipate, cetyl alcohol, benzyl alcohol, and propylene glycol dicaprate, a polyhydric alcohol, and ethanol.

8 Claims, 2 Drawing Sheets

TRANSDERMALLY ABSORBABLE PREPARATION

TECHNICAL FIELD

This invention relates to a transdermally absorbable preparation containing a natural type sex hormone. This invention particularly relates to a natural type sex hormone-containing transdermally absorbable preparation, which is stable and has excellent skin permeation of the natural type sex hormone.

BACKGROUND ART

As hormone replacement therapy, various kinds of sex hormones have heretofore been administered in the forms of oral preparations, injection preparations, transdermal preparations, and the like, as in the cases of the administration of androgen, such as testosterone, for the purpose of improving male hypogonadism, and the administration of a female sex hormone, such as estrogen (estradiol, or the like) or progestogen (progesterone, or the like) for the purpose of improving menopausal disorders and osteoporosis of females or preventing conception. Also, dehydroepiandrosterone, which is a precursor of androgen and estrogen, has heretofore been used clinically as a treatment medicine for adrenalism and systemic lupus erythematosus.

In the sex hormone replacement therapy, a natural type sex hormone, which is biosynthetically produced in a living organism, and a synthetic sex hormone, which is synthesized artificially, are used. In cases where the natural type sex hormone is administered orally, absorption from the digestive canal is scarce, and metabolism in the liver is markedly quick. Therefore, it is necessary for the natural type sex hormone to be administered at a high dose and a plurality of times. Particularly, in the cases of the oral administration of progesterone, which is the natural type progestogen, since bioavailability is markedly low, intramuscular injections, and the like, which impose a heavy burden on patients, are employed as principal administration routes. Recently, various kinds of synthetic type sex hormones, whose pharmacological activity, stability, and the like, have been enhanced over the natural type sex hormone, have been developed, and oral preparations containing the synthetic type sex hormones have been marketed. However, uneasiness has increased about side effects of the administration of the synthetic sex hormones, such as the increase of the risk of breast cancer, and the like, due to the long-term use of the synthetic sex hormones in the hormone replacement therapy. From the view point of risks and benefits, the method using the natural type sex hormone so as to replace the natural type sex hormone that is present in the living organism and that has become insufficient, which method is the original form of the sex hormone replacement therapy, has again attracted particular attention.

Since the bioavailability of the natural type sex hormone by the oral administration is markedly low as described above, in order for the first-pass effect in the liver to be avoided, a transdermally absorbable preparation containing progesterone, estradiol, or the like, has been developed (reference may be made to, for example, non-patent literature 1). However, a satisfactory formulation which brings about sufficiently high and long-acting transdermal absorption such that a systemic effect aiming at the hormone replacement therapy is obtained has not yet been obtained. For example, since progesterone is metabolized even in a skin by 5α-reductase present in the skin, in order for progesterone in a quantity effective for treatment to be delivered from the skin for the purpose of the systemic effect, a markedly high skin permeation rate and the keeping thereof are necessary.

In order for the transdermal absorption of an active drug to be enhanced, there have been made various attempts, such as devising of a form of the administered preparation and the use of a skin permeation enhancer. For example, in patent literatures 1 and 2, transdermal patches containing progesterone or estrogen are described. Also, in patent literatures 3 and 4, transdermal formulations containing estrogen or progesterone, in which specific skin permeation enhancement agents are contained, are described. Further, in patent literature 5, a gel formulation, in which a specific hydrophilic copolymer, a polyhydric alcohol, and an active drug, such as progesterone or estradiol, are contained, is described.

However, the patches have the problems in that, since the drugs must ordinarily be contained with comparatively high concentrations in the preparations for obtaining the systemic effect, and the hormone replacement therapy ordinarily requires the treatment over a long period of time, eruptions of the skins, and the like, occur, and in that, since it is necessary for removal of body hairs to be performed with respect to certain patients, compliance decreases.

Also, as for the preparations in which the skin permeation enhancers are contained, there is the risk of the problems occurring with regard to the side effect, such as skin irritation, and the safety. Further, since the majority of the permeation enhancers increase the solubility of the natural type sex hormones acting as the active ingredients, but decrease thermodynamical activity of the active ingredients on the skins after being applied, expectedly large permeation enhancement effects have not yet been obtained.

Ordinarily, in order for the permeation rate of the drug to be increased in the process of the skin permeation of the drug from a transdermal formulation, it is necessary that the thermodynamical activity of the drug on the skin after being applied is increased, and that the drug solubility in the skin barrier primarily constituted of the stratum corneum is increased. Also, from the view point of the preparation stability and appearance, it is necessary that a sufficient drug solubility in the preparation is obtained. With the conventional techniques, particularly with respect to the hydrophobic drug, such as progesterone, a large quantity of a solvent is required for obtaining the sufficient solubility in the preparation. However, the acquisition of the drug solubility in the preparation by the containing of the large quantity of the solvent decreases the thermodynamical activity of the drug on the skin after being applied and, consequently, could not bring about the sufficient and long-acting skin permeation of the drug.

Patent Literature 1:
  Japanese Patent No. 3086288
Patent Literature 2:
  PCT International Patent Publication No. WO 96/15776
Patent Literature 3:
  Japanese Unexamined Patent Publication No. 10 (1998)-72351
Patent Literature 4:
  PCT Japanese Publication No. 2001-505930
Patent Literature 5:
  Japanese Unexamined Patent Publication No. 9 (1997)-176049
Non-Patent Literature 1:
  Menopause, Vol. 12, No. 2, pp. 232-237, 2005

DISCLOSURE OF INVENTION

Problems which the Invention Aims at Solving

In view of the above circumstances, the object of the present invention is to provide a transdermally absorbable preparation containing a natural type sex hormone, wherein the natural type sex hormone is retained stably in the transdermally absorbable preparation, skin permeation is increased, and a systemic effect and a long-acting property are thereby increased.

Means for Solving the Problems

The inventors eagerly studied for solving the aforesaid problems and found that, in cases where a polyoxyethylene oleyl ether having a molar number of ethylene oxide units added of 20, at least two kinds of oily ingredients selected from the group consisting of diisopropyl adipate, cetyl alcohol, benzyl alcohol, and propylene glycol dicaprate, a polyhydric alcohol, and ethanol are contained with combination together with a natural type sex hormone, while sufficient solubility of the natural type sex hormone in the preparation is being acquired, high thermodynamical activity of the natural type sex hormone on skin after being applied is kept, and long-acting and high transdermal absorption of the natural type sex hormone is brought about. The present invention is based upon the findings described above.

The present invention provides a transdermally absorbable preparation, comprising:

i) a natural type sex hormone acting as an active ingredient,
ii) a polyoxyethylene oleyl ether having a molar number of ethylene oxide units added of 20,
iii) at least two kinds of oily ingredients selected from the group consisting of diisopropyl adipate, cetyl alcohol, benzyl alcohol, and propylene glycol dicaprate,
iv) a polyhydric alcohol, and
v) ethanol.

By the formulation described above, the natural type sex hormone is stably retained in the preparation, and the high skin permeation of the natural type sex hormone is brought about.

The transdermally absorbable preparation in accordance with the present invention should preferably be modified such that the preparation further contains at least one kind of a polyoxyethylene oleyl ether having a molar number of ethylene oxide units added falling within the range of 2 to 10. In cases where the polyoxyethylene oleyl ether having a molar number of ethylene oxide units added of 20 and the polyoxyethylene oleyl ether having a molar number of ethylene oxide units added falling within the range of 2 to 10 are contained with combination in the formulation described above, the skin permeation of the natural type sex hormone is increased even further, and the preparation is stabilized even further.

Also, the transdermally absorbable preparation in accordance with the present invention should preferably be modified such that the natural type sex hormone contains at least one kind of hormone selected from the group consisting of progesterone, estradiol, estrone, estriol, testosterone, and dehydroepiandrosterone, should more preferably be modified such that the natural type sex hormone contains progesterone, and should most preferably be modified such that the natural type sex hormone contains progesterone and estradiol in combination.

Further, the transdermally absorbable preparation in accordance with the present invention should preferably be modified such that the polyhydric alcohol is selected from the group consisting of 1,3-butylene glycol and propylene glycol. By the use of the polyhydric alcohol, the natural type sex hormone is retained more stably.

Furthermore, the transdermally absorbable preparation in accordance with the present invention should preferably be modified such that a containing quantity of ethanol falls within the range of 20% by mass to 60% by mass with respect to the total mass of the preparation.

Effects of the Invention

With the transdermally absorbable preparation in accordance with the present invention, the natural type sex hormone is retained stably in the preparation. Also, in cases where the transdermally absorbable preparation in accordance with the present invention is applied to the skin, the long-acting and high transdermal absorption of the natural type sex hormone is brought about. Therefore, even in cases where the transdermally absorbable preparation in accordance with the present invention is applied with a comparatively low dose and in an open applied manner, the efficient and long-acting systemic effect of the natural type sex hormone is brought about. Also, the transdermally absorbable preparation in accordance with the present invention is excellent in usability and stability.

BEST MODE FOR CARRYING OUT THE INVENTION

The best mode for carrying out the present invention will hereinbelow be described in detail.

The transdermally absorbable preparation in accordance with the present invention contains the natural type sex hormone as the active ingredients.

The natural type sex hormone is one kind of a steroid hormone and embraces natural type androgens and natural type female sex hormones (estrogens and progestogens). Though not limited to a specific hormone, examples of the natural type sex hormones used in the transdermally absorbable preparation in accordance with the present invention include progesterone, estradiol, estrone, estriol, testosterone, and dehydroepiandrosterone. It is sufficient for the sex hormone to be of the natural type, and the sex hormone may be a naturally originating hormone or a synthesized hormone. In the present invention, one kind of the natural type sex hormone may be used alone, or at least two kinds of the natural type sex hormones may be used in combination.

The containing quantity of the natural type sex hormone in the transdermally absorbable preparation in accordance with the present invention varies in accordance with the kind of the natural type sex hormone and the application form, or the like. Though not limited particularly, for example, the containing quantity with respect to the total quantity of the preparation should preferably be 1% by mass to 5% by mass in the cases of progesterone, 0.005% by mass to 2% by mass in the cases of estradiol, and 0.1% by mass to 5% by mass in the cases of each of estrone, estriol, testosterone, and dehydroepiandrosterone. If the containing quantity is lower than the range described above, it will often occur that the long-acting property of the systemic pharmacological effect is not obtained sufficiently with the transdermal application. Also, even if the containing quantity is higher than the range described above, a rise of the effect due to the increase in the containing quantity will not be obtained, and the containing quantity higher than the range described above is not preferable in the aspect of the stability of the preparation.

The transdermally absorbable preparation in accordance with the present invention contains the polyoxyethylene oleyl ether having a molar number of ethylene oxide units added of 20 (hereinbelow referred to as the POE (20) oleyl ether). Though not limited particularly, the containing quantity of the POE (20) oleyl ether should preferably fall within the range of 0.1% by mass to 10% by mass with respect to the total quantity of the transdermally absorbable preparation, and should more preferably fall within the range of 0.5% by mass to 5% by mass with respect to the total quantity of the transdermally absorbable preparation. If the containing quantity is lower than 0.1% by mass, it will often occur that the skin permeation of the active ingredient is not increased sufficiently. Also, the containing quantity higher than 10% by mass is not preferable in the aspect of the safety with respect to the skin.

The transdermally absorbable preparation in accordance with the present invention should preferably further contain at least one kind of the polyoxyethylene oleyl ether having a molar number of ethylene oxide units added falling within the range of 2 to 10. In cases where the POE oleyl ether having a molar number of ethylene oxide units added falling within the range of 2 to 10 is contained with combination with the POE (20) oleyl ether, the skin permeation of the natural type sex hormone is increased even further, and the preparation is stabilized even further. In cases where the POE oleyl ether having a molar number of ethylene oxide units added falling within the range of 2 to 10 is contained, for example, the containing quantity of the POE oleyl ether should preferably fall within the range of 0.1% by mass to 10% by mass with respect to the total quantity of the transdermally absorbable preparation, and should more preferably fall within the range of 0.5% by mass to 5% by mass with respect to the total quantity of the transdermally absorbable preparation.

In so far as the effect of the present invention is not affected adversely, the transdermally absorbable preparation in accordance with the present invention may further contain a POE alkyl ether other than the specific POE oleyl ether described above. However, from the view point of the effect of promoting the skin permeation of the natural type sex hormone and the stability, it is more preferable that the preparation does not contain the POE alkyl ether other than the specific POE oleyl ether described above.

The transdermally absorbable preparation in accordance with the present invention contains at least two kinds of the oily ingredients selected from the group consisting of diisopropyl adipate, cetyl alcohol, benzyl alcohol, and propylene glycol dicaprate. In cases where the aforesaid oily ingredients are contained with combination, the skin permeation of the natural type sex hormone is increased more significantly than in the cases where a different oily ingredient or only one kind of the oily ingredient selected from among the above-enumerated oily ingredients is contained. Also, a stable preparation is obtained. The containing quantity of each of the oily ingredients varies in accordance with the kinds of the oily ingredients used and the combination of the oily ingredients and is not limited particularly. In cases where the oily ingredients are contained, for example, the containing quantity with respect to the total quantity of the transdermally absorbable preparation should preferably be 1% by mass to 10% by mass in the cases of diisopropyl adipate, 1% by mass to 8% by mass in the cases of cetyl alcohol, 1% by mass to 4% by mass in the cases of benzyl alcohol, and 1% by mass to 10% by mass in the cases of propylene glycol dicaprate.

The transdermally absorbable preparation in accordance with the present invention contains the polyhydric alcohol. The polyhydric alcohol used in the present invention is not limited particularly and may be selected from a wide variety of polyhydric alcohols, which are capable of being contained with cosmetic preparations, pharmaceutical preparations, quasi-drugs, and the like. Examples of the polyhydric alcohols, which may be used in the present invention, include propylene glycol, 1,3-butylene glycol, a polyethylene glycol, glycerol, a polyglycerol, and sorbitol. Particularly, 1,3-butylene glycol or propylene glycol is preferable in the aspect of stability of the preparation. Only one kind of the polyhydric alcohol may be used alone, or at least two kinds of the polyhydric alcohols may be used in combination. The containing quantity of the polyhydric alcohol varies in accordance with the kind of the compound used, a desired use feeling, and the like, and is not limited particularly. Ordinarily, the containing quantity of the polyhydric alcohol with respect to the total quantity of the preparation should preferably fall within the range of 1% by mass to 20% by mass, and should more preferably fall within the range of 5% by mass to 15% by mass.

Further, the transdermally absorbable preparation in accordance with the present invention contains ethanol. Though not limited particularly, the containing quantity of ethanol should preferably fall within the range of 20% by mass to 60% by mass, and should more preferably fall within the range of 30% by mass to 50% by mass. If the containing quantity of ethanol is lower than 20% by mass, it will often occur that the stability of the natural type sex hormone and the oily ingredients in the preparation is bad. Also, the containing quantity higher than 60% by mass is not preferable in the aspect of the safety with respect to the skin.

In so far as the transdermally absorbable preparation in accordance with the present invention is prepared as a transdermal preparation, the form of the preparation is not limited particularly and may take on an arbitrary preparation form, such as a gel preparation, a cream preparation, an ointment preparation, a spray preparation, and a liquid preparation. From the view point of the usability, the preparation should preferably be a semi-solid preparation, and should preferably be the gel preparation. Also, the transdermally absorbable preparation in accordance with the present invention may be carried or laminated on an arbitrary support.

If necessary, besides the essential ingredients described above, other arbitrary ingredients, which are ordinarily used in the transdermal preparation, such as the cosmetic preparations and the pharmaceutical preparations, may be contained appropriately with the transdermally absorbable preparation in accordance with the present invention. Also, the transdermally absorbable preparation in accordance with the present invention may be produced by a conventional procedure in accordance with the preparation form to be obtained. For example, the transdermally absorbable preparation in accordance with the present invention may be prepared by a procedure wherein the natural type sex hormone is mixed with and dissolved in the polyoxyethylene oleyl ether, the oily ingredients, the polyhydric alcohol, and ethanol, and wherein the resulting solution is homogeneously mixed with an aqueous phase ingredient containing an aqueous ingredient, such as a water-soluble polymer, dissolved in purified water. Depending upon the kind of the water-soluble polymer used, the resulting mixture may be neutralized by further mixing an alkali.

Examples of the other arbitrary ingredients, which may be contained appropriately, besides the essential ingredients described above, in the transdermally absorbable preparation in accordance with the present invention, include hydrocarbons (such as petrolatum, liquid paraffin, and squalane), aliphatic acid esters (such as isopropyl myristate and diethyl sebacate), higher alcohols, surface-active agents, silicone oils, inorganic powders (such as synthetic sodium magnesium silicate), water-soluble polymers (such as carboxyvinyl polymers, hydroxypropyl cellulose, xanthan gum, and sodium hyaluronate), and purified water. Also, for the pH adjustment, besides amines, such as diisopropanolamine and triethanolamine, it is possible to use inorganic acids (such as hydrochloric acid and phosphoric acid), inorganic bases (such as sodium hydroxide), and the like. Further, if necessary, anti-oxidants, chelating agents, antiseptic agents, and the like, may be contained. Furthermore, in so far as the object of the present invention is capable of being accomplished, an arbitrary skin permeation promoting agent may be contained.

The transdermally absorbable preparation in accordance with the present invention may be used as a transdermal preparation for the purpose of the hormone replacement therapy in arbitrary use applications, such as the improvement of the male hypogonadism by use of androgen, such as testosterone; the improvement of the menopausal disorders and the osteoporosis of females or the contraception by use of estradiol, progesterone, or the like; and the treatment of the adrenalism and the systemic lupus erythematosus by use of dehydroepiandrosterone.

EXAMPLES

The present invention will further be illustrated by the following non-limitative examples. The containing quantity is herein expressed in terms of % by mass with respect to the total quantity of the preparation.

Preparations were prepared with formulations listed in Tables 1-1 and 1-2 (Examples 1 to 19) and formulations listed in Tables 1-3 and 1-4 (Comparative Examples 2 to 16). Each of gel-form preparations was prepared by a procedure wherein a natural type sex hormone was mixed with and dissolved in a polyoxyethylene oleyl ether, oily ingredients, a polyhydric alcohol, and ethanol, and wherein the resulting solution was homogeneously mixed with an aqueous phase ingredient containing an aqueous ingredient, such as a water-soluble polymer, dissolved in purified water. In Comparative Example 1, a commercially available progesterone preparation (Progestelle®), supplied by Women's Therapeutic Institute LLC) was used (reference may be made to Menopause, Vol. 12, No. 2, pp. 232-237, 2005)

TABLE 1-1

| Ingredient | Example 1 | Example 2 | Example 3 | Example 4 | Example 5 |
| --- | --- | --- | --- | --- | --- |
| Progesterone | 3.0 | 3.0 | 3.0 | 3.0 | 3.0 |
| Estradiol | 0.1 | 0.1 | 0.1 | 0.1 | 0.1 |
| POE (20) oleyl ether | 3.0 | 5.0 | 8.0 | 1.0 | 3.0 |
| POE (20) cetyl ether | | | | | |
| POE (20) stearyl ether | | | | | |
| POE (20) behenyl ether | | | | | |
| POE (2) oleyl ether | | | | | |
| POE (5) oleyl ether | | | | | |
| POE (7) oleyl ether | | | | | |
| POE (10) oleyl ether | | | | | |
| Diisopropyl adipate | | | | 5.0 | 8.0 |
| Cetyl alcohol | 3.0 | 5.0 | 5.0 | 3.0 | 3.0 |
| Benzyl alcohol | 4.0 | 4.0 | 4.0 | 3.0 | |
| Propylene glycol dicaprate | | | | | |
| Oleyl alcohol | | | | | |
| Lauryl alcohol | | | | | |
| Isopropyl myristate | | | | | |
| Crotamiton | | | | | |
| Lauric acid | | | | | |
| Oleic acid | | | | | |
| Diethylene glycol monoethyl ether | | | | | |
| Butyl urea | | | | | |
| 1,3-Butylene glycol | 10.0 | 10.0 | 10.0 | 10.0 | 10.0 |
| Propylene glycol | | | | | |
| Ethanol (99.5) | 40.0 | 40.0 | 40.0 | 40.0 | 50.0 |
| Carboxyvinyl polymer | 1.0 | 1.0 | 1.0 | 1.0 | 1.0 |
| Hydroxypropyl cellulose | | | | | |
| Diisopropanolamine | 0.2 | 0.2 | 0.2 | 0.2 | 0.2 |
| Purified water | balance | balance | balance | balance | balance |
| Total | 100.0 | 100.0 | 100.0 | 100.0 | 100.0 |
| Presence or absence of crystals | Absent | Absent | Absent | Absent | Absent |

| Ingredient | Example 6 | Example 7 | Example 8 | Example 9 | Example 10 |
| --- | --- | --- | --- | --- | --- |
| Progesterone | 3.0 | 3.0 | 3.0 | 3.0 | 3.0 |
| Estradiol | 0.1 | 0.1 | | | |
| POE (20) oleyl ether | 5.0 | 0.5 | 5.0 | 5.0 | 5.0 |
| POE (20) cetyl ether | | | | | |
| POE (20) stearyl ether | | | | | |
| POE (20) behenyl ether | | | | | |
| POE (2) oleyl ether | | | | 5.0 | 5.0 |
| POE (5) oleyl ether | | | | | |
| POE (7) oleyl ether | | | | | |
| POE (10) oleyl ether | | | 5.0 | | |
| Diisopropyl adipate | 5.0 | | 10.0 | 10.0 | 5.0 |
| Cetyl alcohol | | 5.0 | 3.0 | 3.0 | 3.0 |
| Benzyl alcohol | 4.0 | 4.0 | | | 2.0 |
| Propylene glycol dicaprate | | | | | |
| Oleyl alcohol | | | | | |
| Lauryl alcohol | | | | | |
| Isopropyl myristate | | | | | |

TABLE 1-1-continued

| Ingredient | | | | | |
|---|---|---|---|---|---|
| Crotamiton | | | | | |
| Lauric acid | | | | | |
| Oleic acid | | | | | |
| Diethylene glycol monoethyl ether | | | | | |
| Butyl urea | | | | | |
| 1,3-Butylene glycol | 10.0 | 10.0 | 10.0 | | 10.0 |
| Propylene glycol | | | | 10.0 | |
| Ethanol (99.5) | 40.0 | 40.0 | 40.0 | 40.0 | 40.0 |
| Carboxyvinyl polymer | 1.0 | 1.0 | 1.0 | 1.0 | 1.0 |
| Hydroxypropyl cellulose | | | | | |
| Diisopropanolamine | 0.2 | 0.2 | 0.2 | 0.2 | 0.2 |
| Purified water | balance | balance | balance | balance | balance |
| Total | 100.0 | 100.0 | 100.0 | 100.0 | 100.0 |
| Presence or absence of crystals | Absent | Absent | Absent | Absent | Absent |

POE: Polyoxyethylene (numeral in parenthesis: molar number of ethylene oxide units added)
Carboxyvinyl polymer: Carbopol (registered trademark) 974P NF

TABLE 1-2

| Ingredient | Example 11 | Example 12 | Example 13 | Example 14 | Example 15 |
|---|---|---|---|---|---|
| Progesterone | 5.0 | 5.0 | 3.0 | 3.0 | 3.0 |
| Estradiol | | | 0.1 | 0.1 | 0.1 |
| POE (20) oleyl ether | 5.0 | 5.0 | 5.0 | 5.0 | 5.0 |
| POE (20) cetyl ether | | | | | |
| POE (20) stearyl ether | | | | | |
| POE (20) behenyl ether | | | | | |
| POE (2) oleyl ether | 5.0 | 5.0 | 1.0 | | |
| POE (5) oleyl ether | | | | | 5.0 |
| POE (7) oleyl ether | | | | | |
| POE (10) oleyl ether | | | | | |
| Diisopropyl adipate | 10.0 | | 5.0 | 5.0 | 5.0 |
| Cetyl alcohol | | | 3.0 | 3.0 | 3.0 |
| Benzyl alcohol | 4.0 | 4.0 | 2.0 | 2.0 | 2.0 |
| Propylene glycol dicaprate | | 5.0 | | | |
| Oleyl alcohol | | | | | |
| Lauryl alcohol | | | | | |
| Isopropyl myristate | | | | | |
| Crotamiton | | | | | |
| Lauric acid | | | | | |
| Oleic acid | | | | | |
| Diethylene glycol monoethyl ether | | | | | |
| Butyl urea | | | | | |
| 1,3-Butylene glycol | 10.0 | 10.0 | 10.0 | 10.0 | 10.0 |
| Propylene glycol | | | | | |
| Ethanol (99.5) | 40.0 | 40.0 | 40.0 | 40.0 | 40.0 |
| Carboxyvinyl polymer | 1.0 | 1.0 | 1.0 | 1.0 | 1.0 |
| Hydroxypropyl cellulose | | | | | |
| Diisopropanolamine | 0.2 | 0.2 | 0.2 | 0.2 | 0.2 |
| Purified water | balance | balance | balance | balance | balance |
| Total | 100.0 | 100.0 | 100.0 | 100.0 | 100.0 |
| Presence or absence of crystals | Absent | Absent | Absent | Absent | Absent |

| Ingredient | Example 16 | Example 17 | Example 18 | Example 19 |
|---|---|---|---|---|
| Progesterone | 3.0 | 3.0 | 3.0 | 3.0 |
| Estradiol | 0.1 | 0.1 | | 0.006 |
| POE (20) oleyl ether | 5.0 | 5.0 | 5.0 | 5.0 |
| POE (20) cetyl ether | | | | |
| POE (20) stearyl ether | | | | |
| POE (20) behenyl ether | | | | |
| POE (2) oleyl ether | | 3.0 | 5.0 | 5.0 |
| POE (5) oleyl ether | | | | |
| POE (7) oleyl ether | 5.0 | | | |
| POE (10) oleyl ether | | | | |
| Diisopropyl adipate | 5.0 | 5.0 | | |
| Cetyl alcohol | 3.0 | 5.0 | | |
| Benzyl alcohol | 2.0 | 2.0 | 2.0 | 2.0 |
| Propylene glycol dicaprate | | | 5.0 | 5.0 |
| Oleyl alcohol | | | | |
| Lauryl alcohol | | | | |
| Isopropyl myristate | | | | |
| Crotamiton | | | | |

TABLE 1-2-continued

| Ingredient | | | | |
|---|---|---|---|---|
| Lauric acid | | | | |
| Oleic acid | | | | |
| Diethylene glycol monoethyl ether | | | | |
| Butyl urea | | | | |
| 1,3-Butylene glycol | 10.0 | 10.0 | 10.0 | 10.0 |
| Propylene glycol | | | | |
| Ethanol (99.5) | 40.0 | 40.0 | 40.0 | 40.0 |
| Carboxyvinyl polymer | 1.0 | 1.0 | 1.0 | 1.0 |
| Hydroxypropyl cellulose | | | | |
| Diisopropanolamine | 0.2 | 0.2 | 0.2 | 0.2 |
| Purified water | balance | balance | balance | balance |
| Total | 100.0 | 100.0 | 100.0 | 100.0 |
| Presence or absence of crystals | Absent | Absent | Absent | Absent |

POE: Polyoxyethylene (numeral in parenthesis: molar number of ethylene oxide units added)
Carboxyvinyl polymer: Carbopol (registered trademark) 974P NF

TABLE 1-3

| Ingredient | Compar. Example 2 | Compar. Example 3 | Compar. Example 4 | Compar. Example 5 | Compar. Example 6 |
|---|---|---|---|---|---|
| Progesterone | 3.0 | 3.0 | 3.0 | 5.0 | 3.0 |
| Estradiol | | | 0.1 | | |
| POE (20) oleyl ether | | 5.0 | | | |
| POE (20) cetyl ether | | | | | |
| POE (20) stearyl ether | | | | | |
| POE (20) behenyl ether | | | | | |
| POE (2) oleyl ether | 5.0 | 5.0 | 5.0 | 5.0 | 5.0 |
| POE (5) oleyl ether | | | | | |
| POE (7) oleyl ether | | | | | |
| POE (10) oleyl ether | | | | | |
| Diisopropyl adipate | 8.0 | | | | 8.0 |
| Cetyl alcohol | | | | | |
| Benzyl alcohol | | | 4.0 | 4.0 | |
| Propylene glycol dicaprate | | | | 5.0 | |
| Oleyl alcohol | | | | | 5.0 |
| Lauryl alcohol | | | | | |
| Isopropyl myristate | | | | | |
| Crotamiton | | | | | |
| Lauric acid | | | | | |
| Oleic acid | | | | | |
| Diethylene glycol monoethyl ether | | | | | |
| Butyl urea | | | | | |
| 1,3-Butylene glycol | 10.0 | 10.0 | 10.0 | 10.0 | 10.0 |
| Propylene glycol | | | | | |
| Ethanol (99.5) | 40.0 | 40.0 | 40.0 | 40.0 | 40.0 |
| Carboxyvinyl polymer | 1.0 | 1.0 | 1.0 | 1.0 | 1.0 |
| Hydroxypropyl cellulose | | | | | |
| Diisopropanolamine | 0.2 | 0.2 | 0.2 | 0.2 | 0.2 |
| Purified water | balance | balance | balance | balance | balance |
| Total | 100.0 | 100.0 | 100.0 | 100.0 | 100.0 |
| Presence or absence of crystals | Absent | Present | Absent | Absent | Absent |

| Ingredient | Compar. Example 7 | Compar. Example 8 | Compar. Example 9 | Compar. Example 10 |
|---|---|---|---|---|
| Progesterone | 3.0 | 3.0 | 3.0 | 3.0 |
| Estradiol | 0.1 | 0.1 | 0.1 | 0.1 |
| POE (20) oleyl ether | 3.0 | | | |
| POE (20) cetyl ether | | 5.0 | | |
| POE (20) stearyl ether | | | 5.0 | |
| POE (20) behenyl ether | | | | 5.0 |
| POE (2) oleyl ether | | | | |
| POE (5) oleyl ether | | | | |
| POE (7) oleyl ether | | | | |
| POE (10) oleyl ether | | | | |
| Diisopropyl adipate | | 5.0 | 5.0 | 5.0 |
| Cetyl alcohol | | | | |
| Benzyl alcohol | 4.0 | 4.0 | 4.0 | 4.0 |
| Propylene glycol dicaprate | | | | |
| Oleyl alcohol | | | | |
| Lauryl alcohol | | | | |
| Isopropyl myristate | | | | |
| Crotamiton | | | | |

TABLE 1-3-continued

| Ingredient | | | | |
|---|---|---|---|---|
| Lauric acid | | | | |
| Oleic acid | | | | |
| Diethylene glycol monoethyl ether | | | | |
| Butyl urea | | | | |
| 1,3-Butylene glycol | 10.0 | 10.0 | 10.0 | 10.0 |
| Propylene glycol | | | | |
| Ethanol (99.5) | 40.0 | 40.0 | 40.0 | 40.0 |
| Carboxyvinyl polymer | 1.0 | 1.0 | 1.0 | 1.0 |
| Hydroxypropyl cellulose | | | | |
| Diisopropanolamine | 0.2 | 0.2 | 0.2 | 0.2 |
| Purified water | balance | balance | balance | balance |
| Total | 100.0 | 100.0 | 100.0 | 100.0 |
| Presence or absence of crystals | Absent | Absent | Absent | Absent |

POE: Polyoxyethylene (numeral in parenthesis: molar number of ethylene oxide units added)
Carboxyvinyl polymer: Carbopol (registered trademark) 974P NF

TABLE 1-4

| Ingredient | Compar. Example 11 | Compar. Example 12 | Compar. Example 13 | Compar. Example 14 | Compar. Example 15 | Compar. Example 16 |
|---|---|---|---|---|---|---|
| Progesterone | 3.0 | 3.0 | 3.0 | 3.0 | 3.0 | 3.0 |
| Estradiol | 0.1 | 0.1 | 0.1 | 0.1 | 0.1 | 0.006 |
| POE (20) oleyl ether | 1.0 | | | | | |
| POE (20) cetyl ether | | | | | | |
| POE (20) stearyl ether | | | | | | |
| POE (20) behenyl ether | | | | | | |
| POE (2) oleyl ether | | | | | | |
| POE (5) oleyl ether | | | | | | |
| POE (7) oleyl ether | | | | | | |
| POE (10) oleyl ether | | | | | | |
| Diisopropyl adipate | | | | | | |
| Cetyl alcohol | | | | | | |
| Benzyl alcohol | 3.0 | | | | | |
| Propylene glycol dicaprate | | | | | | |
| Oleyl alcohol | | | | | | |
| Lauryl alcohol | 3.0 | | | | | |
| Isopropyl myristate | 5.0 | | | | | |
| Crotamiton | | 5.0 | | | | |
| Lauric acid | | | 1.0 | | | |
| Oleic acid | | | | | 5.0 | 5.0 |
| Diethylene glycol monoethyl ether | | | 5.0 | | | |
| Butyl urea | | | | 6.0 | | |
| 1,3-Butylene glycol | 10.0 | | | 20.0 | 10.0 | 5.0 |
| Propylene glycol | | | | | | |
| Ethanol (99.5) | 40.0 | 40.0 | 40.0 | 40.0 | 40.0 | 62.0 |
| Carboxyvinyl polymer | 1.0 | 1.0 | 1.0 | 1.0 | 1.0 | |
| Hydroxypropyl cellulose | | | | | | 1.0 |
| Diisopropanolamine | 0.2 | 0.2 | 0.2 | 0.2 | 0.2 | |
| Purified water | balance | balance | balance | balance | balance | balance |
| Total | 100.0 | 100.0 | 100.0 | 100.0 | 100.0 | 100.0 |
| Presence or absence of crystals | Absent | Absent | Absent | Absent | Absent | Absent |

POE: Polyoxyethylene (numeral in parenthesis: molar number of ethylene oxide units added)
Carboxyvinyl polymer: Carbopol (registered trademark) 974P NF With respect to each of the preparations, confirmation was made with the naked eyes as to whether crystal deposition had or had not occurred. As for the preparation obtained in Comparative Example 3, the crystal deposition was found. As for each of the other preparations, the crystal deposition was not found.

Evaluation of Skin Permeation of Progesterone in In Vitro Skin Permeation Test

With respect to each of the preparations obtained in Examples 1 to 17, Comparative Example 1 (Progestelle®), and Comparative Examples 2 to 15, the skin permeation of progesterone in each preparation was evaluated by the in vitro skin permeation test using a rat abdominal hair-removed and isolated skin as described below.

(Method)

After dermal side binding tissues, and the like, of an abdomen sheared and isolated skin of a six to seven weeks old male rat (IGS type, supplied by Charles River Laboratories Japan) were carefully removed by use of a pair of forceps, the skin was fitted in a 2-chamber type of Franz type diffusion cell (effective permeation area: 3.14 cm$^2$, receiver side volume: 17 ml), such that the stratum corneum might face upward. The test preparation was homogeneously applied on the donor side (the stratum corneum) at a rate of 5 mg per unit area. As a receiver side (dermal side) solution, a mixed solution containing a phosphoric acid buffer having a pH value of 7.4 and polyethylene glycol 400 (in a weight ratio of 70/30) was used. The skin surface temperature was kept at 30° C. by perfusing water having a temperature of 37° C. to the chamber of the diffusion cell. The donor side was kept in an unclosed state, and 1 ml of the receiver solution was collected at each of stages after two, four, six, eight, ten, and 24 hours had elapsed, while the receiver solution was being stirred by use of a magnetic stirrer. The concentration of progesterone in the collected receiver solution was measured by use of high-performance liquid chromatography. A cumulative permeation quantity of progesterone toward the receptor side was calculated from the measured value of the concentration of progesterone, the cumulative amount permeated was plotted with respect to the time, and an apparent steady-state permeation rate ($\mu g/cm^2/h$) of progesterone per unit area was calculated from the slope of the straight line section.

FIG. 1 shows a skin permeation rate of progesterone obtained with respect to each of preparations (n=3, mean±S.D.). Each of the preparations obtained in Examples 1 to 17, which contained the POE (20) oleyl ether, at least two kinds of the oily ingredients selected from the group consisting of diisopropyl adipate, cetyl alcohol, benzyl alcohol, and propylene glycol dicaprate, the polyhydric alcohol, and ethanol together with progesterone, brought about a markedly higher skin permeation rate of progesterone than each of the preparation used in Comparative Example 1, which was the commercially available progesterone preparation, and the preparations obtained in Comparative Examples 2 to 15, which did not contain the combination of the specific oily ingredients described above or the POE (20) oleyl ether.

Evaluation of Transdermal Absorption of Progesterone in In Vivo Single-Dose Administration Test With respect to each of the preparations obtained in Example 18, Comparative Example 1 (Progestelle®), and Comparative Example 16, a concentration of progesterone in blood plasma was measured by performing an in vivo single-dose administration test with the method described below, and the transdermal absorption of progesterone was evaluated with respect to each of the preparations.

(Method)

On the day before the test, the dorsal section of a six weeks old male rat (IGS type, supplied by Charles River Laboratories Japan) was sheared with a clipper and shaved with a shaver. On the day of the test, 200 mg of the test preparation was homogeneously applied over a range of 4×5 cm of the dorsal section, and the dorsal section was kept in an unclosed state. At each of stages of 0.5, one, two, four, eight, and 24 hours after the test was begun, 200 µl of blood was collected from the subclavian vein. With respect to each of the blood samples having thus been obtained, the concentration of progesterone in blood plasma was measured with LC/MS by use of 100 µl of blood plasma.

FIG. 2 shows a change of a concentration of progesterone in blood plasma obtained with respect to each of preparations (n=2 to 4, mean±S.D.). The preparation obtained in Example 18 in accordance with the present invention brought about a markedly higher and longer-acting transdermal absorption of progesterone than each of the preparation (Progestelle®) used in Comparative Example 1, which was the commercially available progesterone preparation, and the preparation obtained in Comparative Example 16.

Evaluation of Transdermal Absorption of Progesterone in In Vivo Repeat-Dose Administration Test With respect to each of the preparations obtained in Example 18, Comparative Example 1 (Progestelle®), and Comparative Example 16, a change of the concentration of progesterone in blood plasma with repeat-dose administration was measured by performing an in vivo repeat-dose administration test with the method described below, and the transdermal absorption of progesterone was evaluated with respect to each of the preparations.

(Method)

On the day before the test, the dorsal section of a six weeks old male rat (IGS type, supplied by Charles River Laboratories Japan) was sheared with a clipper and shaved with a shaver. On the day of the test, 200 mg of the test preparation was homogeneously applied over a range of 4×5 cm of the dorsal section, and the dorsal section was kept in an unclosed state. At a stage after 24 hours had elapsed, 200 µl of blood was collected from the subclavian vein. Further, the application and the blood collection described above were repeated at intervals of 24 hours, and the blood collection was performed at each of stages after 48, 72, and 96 hours had elapsed. With respect to each of the blood samples having thus been obtained, the concentration of progesterone in blood plasma was measured with LC/MS by use of 100 µl of blood plasma. With respect to the blood samples having thus been obtained at the stages after 24, 48, 72, and 96 hours had elapsed, a mean value of the concentrations of progesterone in blood plasma, i.e. the mean value (the mean trough concentration in blood plasma) (ng/ml) of the trough values (the lowest concentrations in blood plasma just before the respective administrations at the time of the repeat-dose administration), was calculated. The trough value is appropriate for the monitoring at the time of the repeat-dose administration of a drug and is utilized for the evaluation of the effect and a side effect.

Table 2 below shows the mean trough concentration in blood plasma obtained with respect to each of the preparations (n=4, mean±S.D.).

TABLE 2

Evaluation of transdermal absorption of progesterone in in vivo repeat-dose administration test

| Test preparation | Mean trough concentration of progesterone in blood plasma (ng/ml) |
| --- | --- |
| Example 18 | 8.1 ± 1.8 |
| Comparative Example 1 (Progestelle (registered trademark)) | 1.2 ± 0.1 |
| Comparative Example 16 | 1.4 ± 0.1 |

The preparation obtained in Example 18 in accordance with the present invention kept a markedly higher concentration of progesterone in blood plasma with the repeat-dose administration than each of the preparation (Progestelle®) used in Comparative Example 1, which was the commercially available progesterone preparation, and the preparation obtained in Comparative Example 16.

Evaluation of Transdermal Absorption of Estradiol in In Vivo Single-Dose Administration Test With respect to each of the preparations obtained in Example 19 and Comparative Example 16, the concentration of estradiol in blood plasma was measured by performing an in vivo single-dose administration test with the method described below, and the transdermal absorption of estradiol was evaluated with respect to each of the preparations.

(Method)

As estradiol, [6,7-$^3$H(N)]-estradiol (43.8 mCi/mmol, supplied by PerkinElmer, Inc.) was used. A test preparation was prepared such that specific radioactivity in the test preparation might be 9 MBq/g (estradiol: 0.006% by mass). On the day before the test, the dorsal section of a six weeks old male rat (IGS type, supplied by Charles River Laboratories Japan)

was sheared with a clipper and shaved with a shaver. On the day of the test, 200 mg of the test preparation was homogeneously applied over a range of 4×5 cm of the dorsal section, and the dorsal section was kept in an unclosed state. At each of stages of 0.5, one, two, four, eight, and 24 hours after the test was begun, 100 μl of blood was collected from the subclavian vein. With respect to each of the blood samples having thus been obtained, treatment with a sample oxidizer (supplied by Hewlett-Packard Company) was performed, and radioactivity was measured with a liquid scintillation counter.

Table 3 below shows a mean radioactive concentration (pg eq./ml) of estradiol in blood plasma obtained with respect to each of the preparations at the stage of 24 hours after the administration (n=2).

TABLE 3

Evaluation of transdermal absorption of estradiol in in vivo single-dose administration test

| Test preparation | Mean radioactive concentration in blood plasma at the stage of 24 hours after the administration (pg eq./ml) |
|---|---|
| Example 19 | 512 |
| Comparative Example 16 | 340 |

The preparation obtained in Example 19 in accordance with the present invention brought about a significantly higher transdermal absorption of estradiol than the preparation obtained in Comparative Example 16.

Examples illustrating the formulation of the transdermally absorbable preparation in accordance with the present invention, which contains the natural type sex hormone as the active ingredient, will further be described below. In each of Examples, the containing quantity is expressed in terms of % by mass with respect to the total quantity of the formulations.

Example 20

| Ingredient | Containing quantity (% by mass) |
|---|---|
| Progesterone | 3.0 |
| Dehydroepiandrosterone | 1.0 |
| Polyoxyethylene (20) oleyl ether | 5.0 |
| Polyoxyethylene (7) oleyl ether | 5.0 |
| Benzyl alcohol | 2.0 |
| Diisopropyl adipate | 5.0 |
| Cetyl alcohol | 3.0 |
| 1,3-Butylene glycol | 10.0 |
| Ethanol (99.5) | 40.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Example 21

| Ingredient | Containing quantity (% by mass) |
|---|---|
| Testosterone | 1.0 |
| Polyoxyethylene (20) oleyl ether | 5.0 |
| Polyoxyethylene (2) oleyl ether | 3.0 |
| Benzyl alcohol | 2.0 |
| Diisopropyl adipate | 5.0 |
| Cetyl alcohol | 1.0 |
| 1,3-Butylene glycol | 10.0 |
| Ethanol (99.5) | 40.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Example 22

| Ingredient | Containing quantity (% by mass) |
|---|---|
| Progesterone | 3.0 |
| Estrone | 0.5 |
| Polyoxyethylene (20) oleyl ether | 1.0 |
| Polyoxyethylene (5) oleyl ether | 3.0 |
| Benzyl alcohol | 2.0 |
| Cetyl alcohol | 5.0 |
| 1,3-Butylene glycol | 10.0 |
| Ethanol (99.5) | 50.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Example 23

| Ingredient | Containing quantity (% by mass) |
|---|---|
| Progesterone | 5.0 |
| Testosterone | 0.5 |
| Polyoxyethylene (20) oleyl ether | 5.0 |
| Polyoxyethylene (2) oleyl ether | 3.0 |
| Benzyl alcohol | 4.0 |
| Diisopropyl adipate | 8.0 |
| 1,3-Butylene glycol | 10.0 |
| Ethanol (99.5) | 40.0 |
| Carboxyvinyl polymer (Carbopol (registered trademark) 974P NF) | 1.0 |

-continued

| Ingredient | Containing quantity (% by mass) |
|---|---|
| Diisopropanolamine | 0.2 |
| Purified water | balance |
| Total | 100.0 |

A gel-form preparation having a transparent appearance was obtained.

Example 24

| Ingredient | Containing quantity (% by mass) |
|---|---|
| Progesterone | 3.0 |
| Estriol | 1.0 |
| Polyoxyethylene (20) oleyl ether | 1.0 |
| Polyoxyethylene (5) oleyl ether | 3.0 |
| Benzyl alcohol | 2.0 |
| Diisopropyl adipate | 5.0 |
| Cetyl alcohol | 3.0 |
| 1,3-Butylene glycol | 10.0 |
| Ethanol (99.5) | 40.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Example 25

| Ingredient | Containing quantity (% by mass) |
|---|---|
| Progesterone | 3.0 |
| Estradiol | 0.1 |
| Polyoxyethylene (20) oleyl ether | 5.0 |
| Polyoxyethylene (5) oleyl ether | 3.0 |
| Benzyl alcohol | 1.0 |
| Cetyl alcohol | 3.0 |
| Propylene glycol dicaprate | 5.0 |
| 1,3-Butylene glycol | 10.0 |
| Ethanol (99.5) | 40.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Example 26

| Ingredient | Containing quantity (% by mass) |
|---|---|
| Dehydroepiandrosterone | 5.0 |
| Polyoxyethylene (20) oleyl ether | 5.0 |
| Polyoxyethylene (5) oleyl ether | 3.0 |
| Benzyl alcohol | 4.0 |
| Diisopropyl adipate | 3.0 |
| Cetyl alcohol | 1.0 |
| 1,3-Butylene glycol | 10.0 |
| Ethanol (99.5) | 40.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Example 27

| Ingredient | Containing quantity (% by mass) |
|---|---|
| Progesterone | 3.0 |
| Estriol | 2.0 |
| Polyoxyethylene (20) oleyl ether | 2.0 |
| Polyoxyethylene (2) oleyl ether | 2.0 |
| Benzyl alcohol | 3.0 |
| Diisopropyl adipate | 5.0 |
| Cetyl alcohol | 3.0 |
| 1,3-Butylene glycol | 10.0 |
| Ethanol (99.5) | 40.0 |
| Carboxyvinyl polymer (Carbopol (registered trademark) 974P NF) | 1.0 |
| Diisopropanolamine | 0.2 |
| Purified water | balance |
| Total | 100.0 |

A gel-form preparation having a transparent appearance was obtained.

Each of the preparations obtained in Examples described above was the stable preparation and brought about the high skin permeation of the natural type sex hormone contained.

Figure 1:
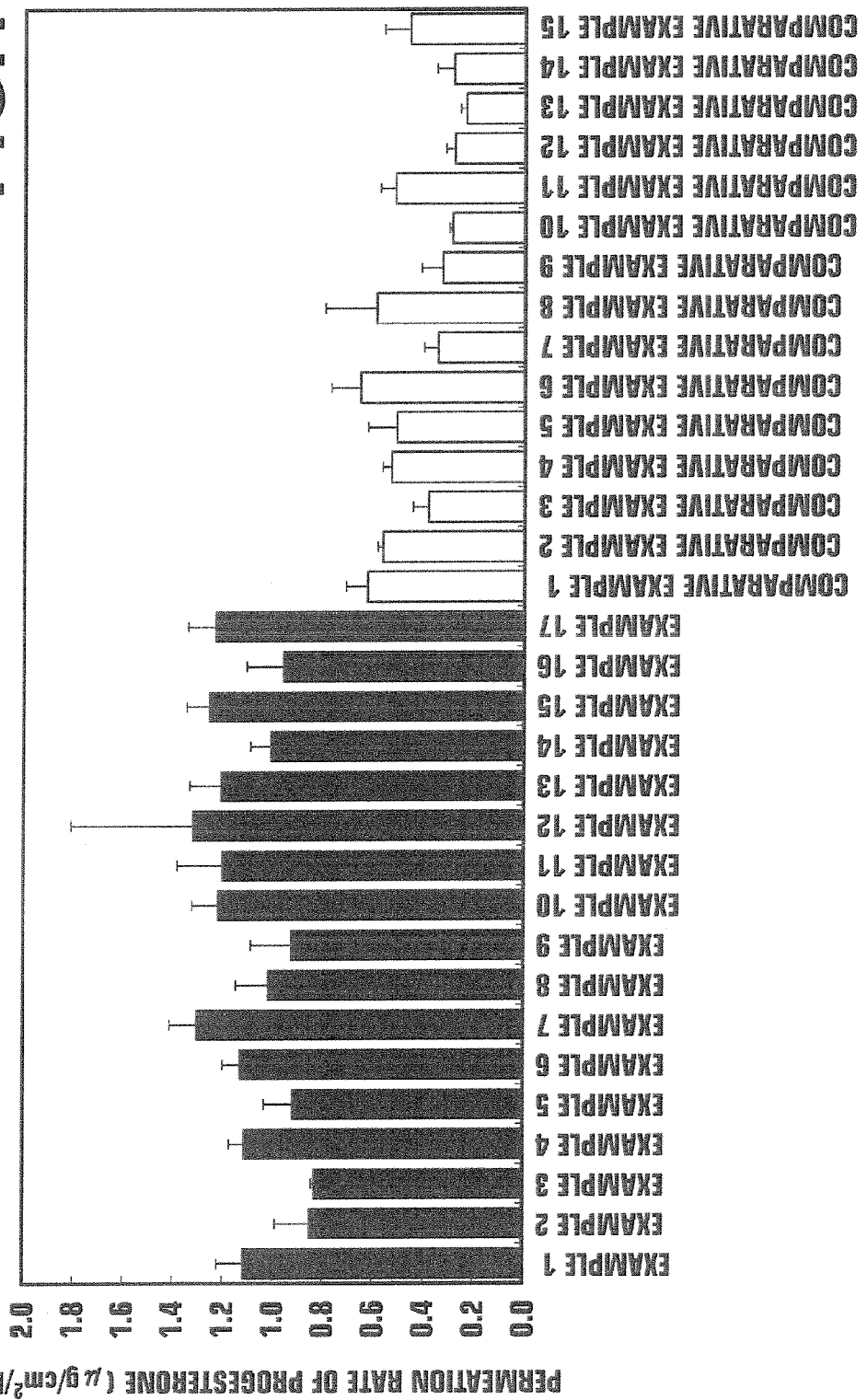
FIG. 1 is a graph showing a skin permeation rate of progesterone obtained with respect to each of preparations in in vitro skin permeation tests.
Figure 2:
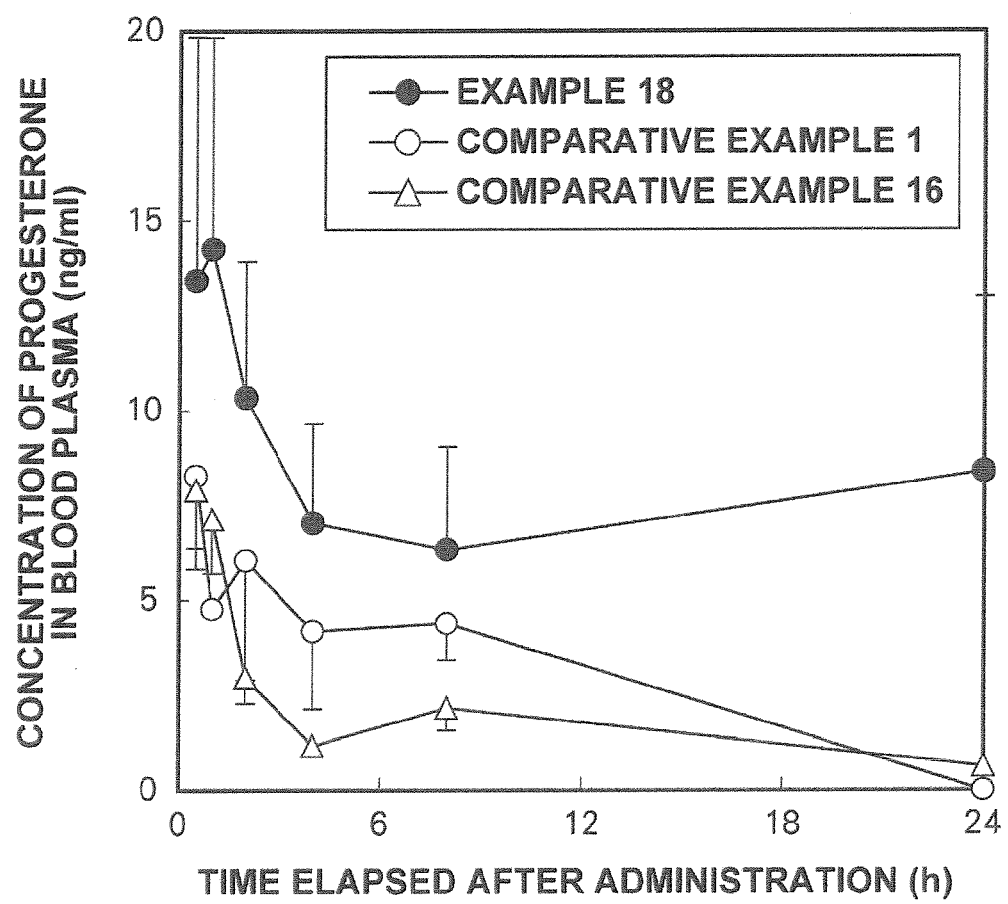
FIG. 2 is a graph showing a change of a concentration of progesterone in blood plasma obtained with respect to each of preparations in in vivo single-dose administration tests.

The invention claimed is:
1. A transdermally absorbable preparation, comprising:
i) at least one selected from the group consisting of progesterone, estradiol, estrone, estriol, testosterone, and dehydroepiandrosterone, ii) a polyoxyethylene oleyl ether having a molar number of ethylene oxide units added of 20,
iii) at least two kinds of oily ingredients selected from the group consisting of diisopropyl adipate, cetyl alcohol, benzyl alcohol, and propylene glycol dicaprate,
iv) a polyhydric alcohol, and
v) ethanol, wherein ethanol is present in an amount of 20% to 60% by mass with respect to the total mass of the preparation.

2. The transdermally absorbable preparation of claim 1, wherein the preparation further contains at least one kind of a polyoxyethylene oleyl ether having a molar number of ethylene oxide units added falling within the range of 2 to 10.

3. The transdermally absorbable preparation of claim 1, wherein the preparation contains progesterone.

4. The transdermally absorbable preparation of claim 3, wherein the preparation further contains estradiol.

5. The transdermally absorbable preparation of claim 2, wherein the preparation contains progesterone.

6. The transdermally absorbable preparation of claim 5, wherein the preparation further contains estradiol.

7. The transdermally absorbable preparation of claim 1, wherein the polyhydric alcohol is selected from the group consisting of 1,3-butylene glycol and propylene glycol.

8. The transdermally absorbable preparation of claim 2, wherein the polyhydric alcohol is selected from the group consisting of 1,3-butylene glycol and propylene glycol.

* * * * *